(12) United States Patent
Prevost et al.

(10) Patent No.: US 7,935,370 B1
(45) Date of Patent: May 3, 2011

(54) USE OF FLOUR CONSISTENCY FEEDSTOCK AND IMPROVED HYDROLYZING CONDITIONS IN AN ETHANOL PRODUCTION PROCESS

(75) Inventors: John E. Prevost, Slaughter, LA (US); Neal A. Hammond, Cameron Park, CA (US)

(73) Assignee: Little Sioux Corn Processors, LLC., Marcus, IA (US)

( * ) Notice: Subject to any disclaimer, the term of this patent is extended or adjusted under 35 U.S.C. 154(b) by 1278 days.

(21) Appl. No.: 11/162,942

(22) Filed: Sep. 28, 2005

Related U.S. Application Data

(63) Continuation-in-part of application No. 10/710,125, filed on Jun. 21, 2004, now abandoned, which is a continuation-in-part of application No. 10/619,822, filed on Jul. 15, 2003, now Pat. No. 7,318,016, which is a continuation-in-part of application No. 10/458,480, filed on Jun. 10, 2003, now Pat. No. 7,300,680, which is a continuation-in-part of application No. 10/395,547, filed on Mar. 24, 2003, now abandoned, which is a continuation-in-part of application No. 10/281,490, filed on Oct. 28, 2002, which is a continuation-in-part of application No. 10/008,834, filed on Nov. 9, 2001, now abandoned, which is a continuation-in-part of application No. 09/229,286, filed on Jan. 13, 1999, now abandoned.

(51) Int. Cl.
*A21D 2/02* (2006.01)

(52) U.S. Cl. ............... 426/46; 426/26; 426/29; 426/11
(58) Field of Classification Search .................. 426/46, 426/26, 29, 11
See application file for complete search history.

(56) References Cited

U.S. PATENT DOCUMENTS

| | | | | |
|---|---|---|---|---|
| 4,361,651 A | * | 11/1982 | Keim | 435/161 |
| 5,231,017 A | * | 7/1993 | Lantero et al. | 435/161 |
| 7,138,257 B2 | * | 11/2006 | Galli et al. | 435/161 |

OTHER PUBLICATIONS

Abstract from Biological Wastes, vol. 30, Issue 2, 1989. Cadoche et al.*

* cited by examiner

*Primary Examiner* — Anthony Weier
(74) *Attorney, Agent, or Firm* — Brown Winick Law Firm

(57) ABSTRACT

An improved process is shown wherein a carbohydrate-containing feedstock, such as corn, is milled to form a flour having a median particle size of less than about 100 microns. The flour is then hydrolyzed along with added vitamins and/or nutrients and/or enzymes. The hydrolyzed product is then mixed with a soy hull flour, also preferably having a median particle size of less than about 100 microns, and subjected to conventional fermentation to produce an ethanol containing product. The ethanol-containing product is then distilled to produce an ethanol enriched steam and a separate whole stillage. In preferred embodiments the process includes various filtration treatments of the whole stillage with and without added vitamins, nutrients, or other compounds to obtain value-added by-products.

18 Claims, 4 Drawing Sheets

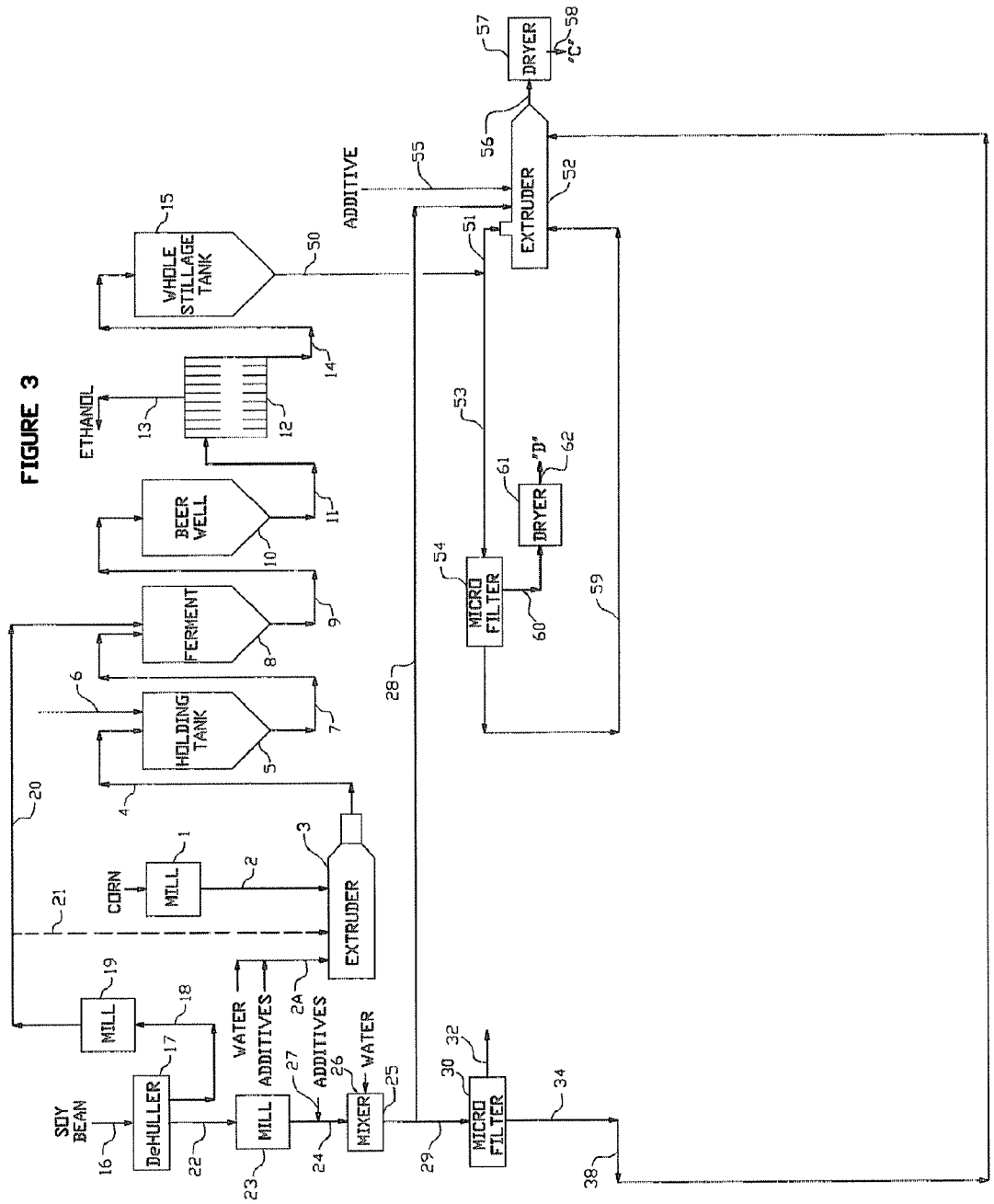

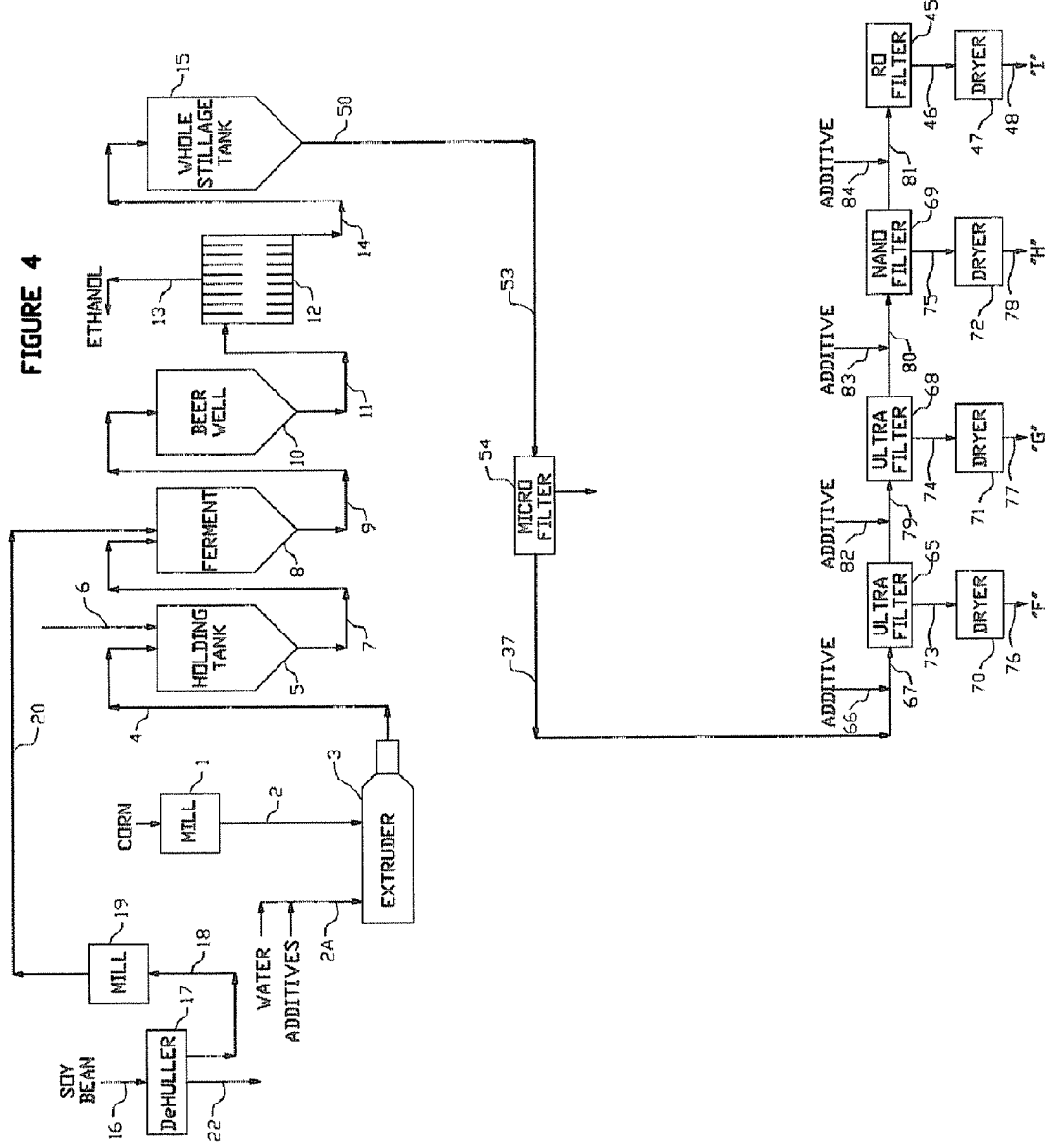

USE OF FLOUR CONSISTENCY FEEDSTOCK AND IMPROVED HYDROLYZING CONDITIONS IN AN ETHANOL PRODUCTION PROCESS

CROSS-REFERENCE TO RELATED APPLICATIONS

This application is a continuation-in-part of U.S. patent application Ser. No. 10/458,480 filed Jun. 10, 2003, which in turn is a continuation of U.S. patent application Ser. No. 10/008,834 filed Nov. 9, 2001, which in turn is a continuation of U.S. patent application Ser. No. 09/229,286 filed on Jan. 13, 1999.

This application is also a continuation-in-part of U.S. patent application Ser. No. 10/710,125 filed Jun. 21, 2004, which is a continuation-in-part of U.S. patent application Ser. No. 10/619,822 filed Jul. 15, 2003, which is a continuation-in-part of U.S. patent application Ser. No. 10/395,547 filed Mar. 24, 2003, which is a continuation-in-part of U.S. patent application Ser. No. 10/281,490 filed Oct. 28, 2002.

BACKGROUND OF THE INVENTION

1. Field of the Invention

This invention relates in general to an ethanol production process, and more particularly to methods of producing ethanol and whole stillage from a carbohydrate containing feedstock, such as corn, with and without a soy based feedstock, such as soybeans, and subsequent treatments of the whole stillage to produce recoverable value-added products.

2. Prior Art

With the ever-increasing depletion of economically recoverable petroleum reserves, as well as the environmental impact of the drilling processes to effect the recovery, the production of ethanol from carbohydrate containing sources as a partial or complete replacement for conventional fossil-based liquid fuels has become more attractive. A variety of materials have been utilized as the starch or sugar-containing feedstock in ethanol producing processes. One of the most common feedstock is whole corn kernels. In a conventional ethanol production process utilizing corn as the initial feedstock, the corn is first ground to produce a milled corn. This is typically achieved by the use of a hammer mill or other similar conventional milling equipment. Water, nutrients, and enzymes are then added to the milled corn to form a liquefied slurry. The liquefied slurry is then mixed in a fermentation vessel with water, yeast, and selected minerals and nutrients, whereby it then undergoes fermentation. The fermented product, commonly referred to as the "beer" is then distilled to produce an ethanol rich stream (about 95% ethanol and 5% water by weight) and a whole stillage, comprising water, as well as the solids resulting from the fermentation, from which by-products are then recoverable. Unfortunately, the by-products obtained from the conventional ethanol producing processes do not have sufficient economic value because of their relative low nutrient content to permit these processes from economically competing with conventional fossil fuel processes. Furthermore, because of the economics involved in the current process, the costs of producing ethanol and other resultant by-products has remained relatively high when compared to the fossil fuel sources, and such ethanol production processes have remained economically viable due mostly to government subsidies. Efforts to improve the economic viability of these processes have been addressed, but there still remains demand for the gain of further economic benefit from the use of an ethanol production process. Further improvements to the ethanol producing process that can either achieve processing cost savings or enhanced value by-products are therefore desirable.

OBJECTS AND SUMMARY OF THE INVENTION

It is an object of the invention to provide an improved ethanol and whole stillage production process that provides processing cost savings.

It is an another object of this invention to provide an improved whole stillage treatment process that results in the production and recovery of value-added products, including nutritional, nutraceutical, flavor enhancing, cosmetic, and/or pharmaceutical products.

It is still another object of this invention to provide a process for treatment of soybeans to produce an improved feedstock for use in an ethanol process, as well as to produce value-added products from the soybeans.

These and other objects and advantages of the invention shall become apparent from the ensuing figures and descriptions of the invention.

Accordingly, an improved process for producing ethanol and whole stillage is disclosed. The carbohydrate containing feedstock, such as whole corn kernels, is first subjected to a milling process to achieve a predetermined and preferred granulation that allows for a more efficient treatment by the subsequent hydrolysis and fermentation steps. In a preferred embodiment the feedstock will be milled to a flour consistency; i.e., having a median particle size of less than about 100 microns. Water and additives, such as nutrients and pre-determined enzymes, are then added to the milled feedstock in a predetermined and preferred ratio to form liquefied slurry. The slurry is then extruded under preferred time, pressure, and temperature conditions that promote the hydrolysis of the corn. The hydrolysis can be performed utilizing any number of known mixing apparatus that can control temperature and pressure of its contents. For example this could include a steam-jacketed pressure mixer operating under pressure. It could also include a steam-jacketed extruder. Particular extruders include a twin screw type extruder, that results in both mixing and hydrolysis of the slurry. The extruded slurry is subsequently subjected to fermentation and then distillation processes carried out under known fermentation and distillation conditions to produce an ethanol rich stream and a whole stillage. In a preferred embodiment the whole stillage will be treated by various filtration steps to recover value-added by-products. In another preferred embodiment, soy materials resulting from the processing of soybeans are added to various phases of the ethanol and whole stillage production and by-product recovery process.

The milling, extrusion, fermentation, and whole stillage treatment methods provided for by the present invention, in conjunction with the utilization of soy additives, result in an overall improved ethanol and by-product production process that achieves processing cost savings and recovery of value-added by-products useful as nutrient supplements for food products, or in the formulation of cosmetic products, and/or neutraceutical products, and/or pharmaceutical products.

BRIEF DESCRIPTION OF THE FIGURES

The accompanying drawings illustrate several preferred embodiments of the invention. However, it is to be understood that these embodiments are not intended to be either exhaustive, or limiting of the invention. They are but examples of some of the forms in which the invention may be practiced.

FIG. 3 is a schematic flow chart illustrating a preferred embodiment of the process utilizing the whole stillage produced by the preferred ethanol process to produce a protein rich nutrition product useful as a food supplement, as well as an oil-protein-carbohydrate rich emulsion product.

FIG. 4 is a schematic flow chart illustrating a preferred embodiment of the process of producing from the whole stillage various value-added products, such as a non-zein corn enriched product, a zein protein enriched product, a cyclodextrin enriched product, and a vitamin, mineral, carbohydrate small molecule enriched product.

DETAILED DESCRIPTION OF THE INVENTION

Without any intent to limit the scope of this invention, reference is made to the Figures in describing the preferred embodiments of the invention.

Although the preferred embodiments of this invention are described utilizing a whole kernel corn feedstock, it is understood that this process can also be carried out utilizing a variety of other carbohydrate-containing materials, such as molasses, bagasse, sugar beets, artichokes, and cereal grains such as barley and wheat. It is also to be understood that alternative protein-containing materials resulting from the processing of other protein-containing feedstocks, such as whey, can be used as additives to the various stages of the process.

Figure 1:
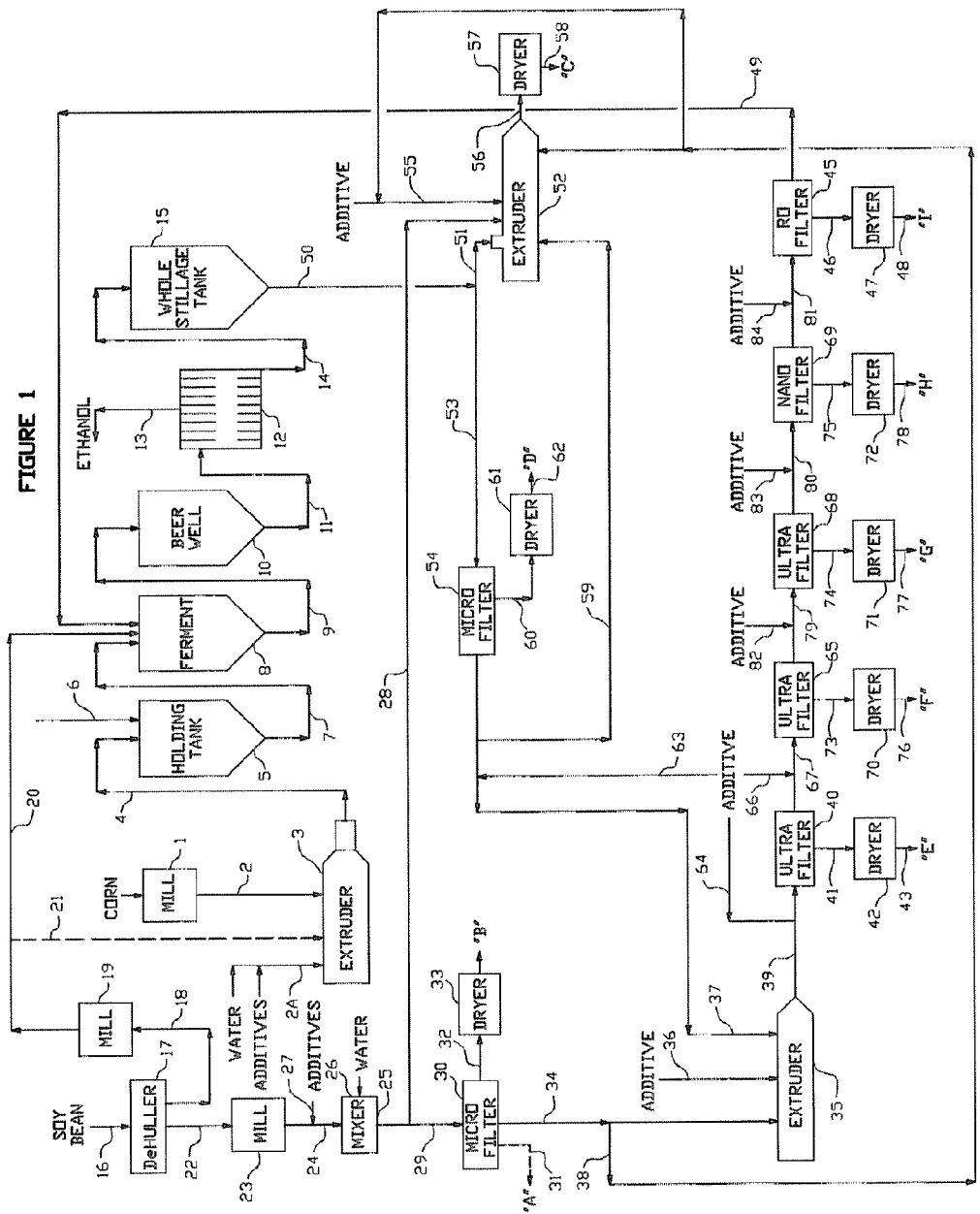
FIG. 1 is a schematic flow chart illustrating an integrated process utilizing both soybean and whole kernel corn feedstocks to produce ethanol and various value-added by-products from the whole stillage and the soybeans.
Figure 2:
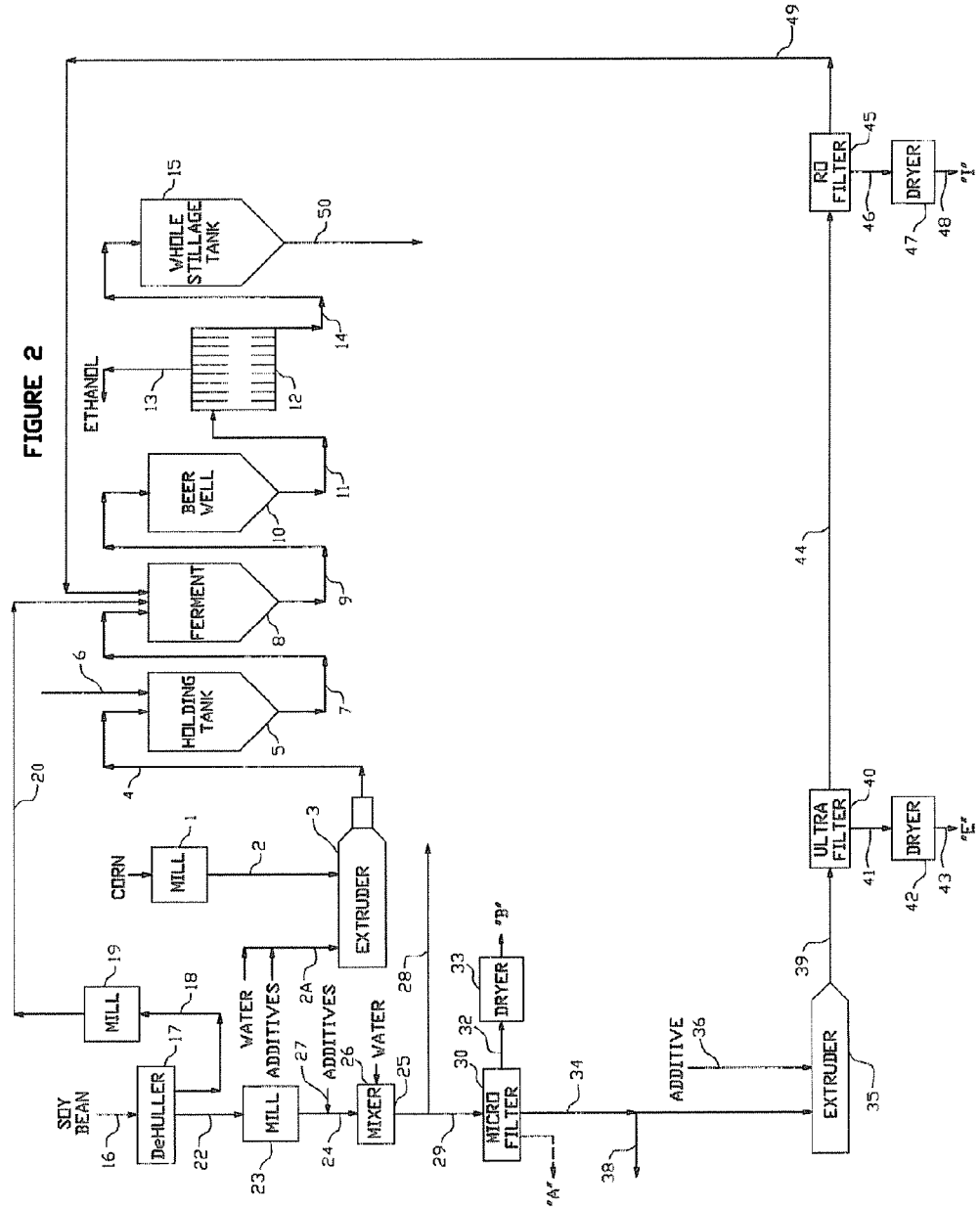
FIG. 2 is a schematic flow chart illustrating a preferred embodiment of the ethanol and whole stillage production process of the present invention utilizing both a soybean and a whole corn kernel feedstock and the production value-added by-products from the soybean feedstock.

Referring now to FIGS. 1 and 2 an integrated soybean and whole corn kernel feedstock process is illustrated that produces ethanol and whole stillage having improved value, as well as, various value-added by-products from the soybeans. In the preferred process whole kernel corn are first cleaned in a washing apparatus in preparation for milling. The washed corn is then feed to mill 1 to reduce the particles size of the kernels and break any outer protective covering, such as the pericap, to expose the inner starch and protein components of the kernel. More preferably the corn will be ground to a flour consistency; i.e., having a median particle size of less than about 100 microns. This novel step results in greater ethanol production efficiency, as well as improves the later filtration treatment of the whole stillage to produce the various value-added by-products possible with this invention. This is a departure from traditional ethanol production process where the corn is ground to a meal consistency in order to allow easier separation of the animal feed by-product in the whole stillage.

The flour will be combined in extruder 2 with water and additives from line 2A to form a slurry. Additives that can form part of the slurry in extruder 3 include enzymes, such as 1% alpha-amylase. Other amylase enzyme types, as well as other enzymes can also be utilized to advantage, depending on the desired by-products to be obtained from the subsequent treatment of the whole stillage. In another novel feature the amount of enzymes added is set at about 0.5% to about 1.5% by dry weight rather than the traditional 0.1% by dry weight. In another aspect of this invention multiple enzymes can be simultaneously used. In this embodiment the enzymes are selected to enable each to perform its function in the same processing environment without interference in the later production of ethanol during the fermentation step. The additives can also include selected nutrients, such as mineral containing compounds, as well as nitrogen containing compounds, such as phosphorus, calcium, and potassium. Preferably the selected nutrients should enhance the rate and efficiency of the subsequent fermentation phase. The amount of water, enzymes and nutrients in the slurry can be varied from about 70% to about 90% by weight of the corn flour. Preferably, the corn flour, water, enzymes, and nutrients are mixed in a ratio of about 100:20:1.5:1 to about 100:15:0.5:0.5 by weight to form the slurry.

The slurry is then mixed and hydrolyzed. Known equipment can be used to achieve these steps. On such equipment is extruder 3 chosen to perform not only the mixing of the corn, water, and additives, but to also perform the hydrolysis of the resulting slurry. Known extruders that can perform this dual task include many commercially available twin screw extruders, such as the Wenger TX-52, the Baker Perkins MPC/V 80, the APV SB80, the Werner & Pfleiderer ZSK-92, the Clextral BC 92, and the Buhler BVTF-93, as well as certain single screw extruders, such as the Anderson 4" extruder.

To promote the hydrolysis of the slurry, the operating conditions of extruder 3 are set to optimize conversions of the starches in the slurry to dextrins. In a preferred embodiment the slurry is subjected to the cooking in extruder 3 for a period of time and under temperature and pressure conditions that result in hydrolytic reactions that partially gelatinize corn flour and cleave the terminal amylose groups of the corn starch molecules. Since the temperature, pressure, and reaction time variables are interrelated, a higher pressure will result in a higher temperature, which in turn, will increase the reaction rate and result in more cleavage. In a preferred embodiment the slurry is extruded under conditions sufficient to cleave at least 20%-40% of the terminal amylase groups from the corn starch molecules, with as many as economically feasible preferably being cleaved. In general, extrusion cooking utilizes the extruder motor driven rotating screws to force a relatively dry mass (e.g., 10%-40% moisture) down the extruder barrel having a plurality of zones with holding tubes situated therebetween. A shaping die located at the outlet of the barrel causes the mass to pressurize and its temperature to rise. The pressure generated can rise to 300-3000 psi, causing the internal temperature to rise above the normal boiling point of water, without the production of steam or loss of moisture. Under such conditions, a cereal-based food mass will heat to 100° C. to 200° C. in less than two seconds and undergo hydrolytic reactions and convert to a homogenous gelatinized mass. In a conventional ethanol production process the hydrolysis is conducted at ambient pressure and at about 105° C. The slurry is maintained under these conditions for about 15 minutes to complete the hydrolysis. However, in this invention it is preferred that the slurry is extruded at moderate pressure (e.g., about 500 psi) for 45-60 seconds, with the temperature conditions ranging from 80° C. to 130° C. Under these conditions and with the use of additional enzymes this phase of the process functions as a catalyst to encourage a faster rate of corn starch hydrolysis and terminal amylase residue production. These terminal amylase residues, in turn, serve a critical function, as they appear to be responsible for the principle fermentation improvement properties of the corn flour hydrolysates, products of corn flour hydrolysis that serve as a fermentation media. This permits a more efficient treatment by the subsequent fermentation step. Browning of the mass can be reduced or eliminated by cooling the ends of the extruder 3 by known methods and apparatus. Necessary pH adjustments to the mass may be made by transferring the mass through line 4 to a holding tank 5 where pH adjustment streams can be added by line 6 and mixed with the homogenous gelatinized mass in tank 5.

The extruded slurry from holding tank 5 is then fed via line 7 to fermentation tank 8 where it undergoes fermentation. Because the ethanol and whole stillage production process of this invention utilizes a finer corn flour product, and further includes an extrusion-cooking phase promoting the hydrolysis of the finer corn flour, the rate of fermentation is more rapid, and the amount of ethanol recovered from the distillation step is greater. As also discussed below, the fermentation rate can further be improved with the addition of soy hull flour to the slurry in fermentation tank 8. Accordingly, the invention provides for a faster and more efficient ethanol and whole stillage production, which in turn, achieves processing cost savings and improves the overall economic viability of the ethanol and whole stillage production process.

After the slurry has undergone fermentation 26, the fermented slurry (aka/liquor or beer) is sent via line 9 to the beer well 10. From beer well 10 the fermented slurry is transported via line 11 to distillation column 12 where under heat and vacuum evaporated ethanol is recovered via line 13. The remaining water containing liquid after ethanol removal is called whole stillage and can be recovered from distillation column 12 via line 14. The whole stillage comprises components native to the corn plant that remained unchanged during the fermentation phase. In addition it comprises components native to the corn plant that underwent modification during the fermentation phase, as well as components added to the fermentation tank to promote the growth of the fermentation organism. It further comprises components that were a part of the fermentation organism, including cell materials, and products of cellular metabolism. The whole stillage is then transferred via line 14 to whole stillage storage tank 15 for further processing as described below to recover value-added by-products.

In another preferred embodiment soy material, preferably from the processing of soybeans, is utilized as additives to various stages of the ethanol and whole stillage production process and as a feedstock in various by-product recovery processes. This embodiment improves processing costs, as well as achieves value-added by-products. It is to be understood that alternative protein-containing materials, resulting from the processing of other protein-containing feedstock, such as whey, can also be utilized as additives to the various stages of the ethanol and whole stillage production and by-product recovery process.

In the preferred embodiment full fat soybeans are feed via line 16 to a conventional de-huller 17 to remove the soybean hulls. The removed soy hulls are then transferred via line 18 to a conventional mill 19 where they are ground to flour consistency; i.e., having a median particle size of less than about 100 microns. This soy hull flour is added to the fermentation tank 8 via line 20 where it is mixed with the extruded slurry to improve the rate of ethanol fermentation and to provide additional nutrients in the resultant whole stillage. In an alternate embodiment at least a portion of the soy hull flour is feed into extruder 3 via line 21 where it is mixed with the corn flour, water, enzymes, and additives, and then extruded.

The de-hulled and full fat soy meal recovered from de-huller 17 is then transferred via line 22 to mill 23 to achieve a soy flour; i.e., having a median particle size of less than about 100 microns. The soy flour is transferred via line 24 to mixer 25 where water from line 26 and additives from line 27 are mixed with the soy flour in mixer 26 to form a full fat soy slurry. The additives can include desired nutrients and enzymes. The selection of nutrients and enzymes is dependent on the desired value-added by-products desired to be recovered from the subsequent process steps.

In a preferred embodiment, a portion of this full fat soy slurry is transferred via line 28 to be combined with the whole stillage to increase the nutritional content of by-product "C" resulting from the extrusion and drying process described below. The remaining portion of the full fat solution is transferred via line 29 to microfiltration unit 30 to produce a defatted soy solution comprising proteins and other nutrients, and a retentate. The defatted soy solution can be recovered via line 31 as value-added by-product "A" that is useful in the formulation of neutraceuticals and in the paint industry for the production of acrylics.

The microfilter size should preferably be set so that the retentate includes soy oil, soy proteins, and soy carbohydrates, all combining to form an emulsion. A filter size of about 0.1 to 1.0 microns is preferred. The soy retentate emulsion is transferred via line 32 to dryer 33 to form value-added by-product "B". The drying conditions are preferably controlled to reduce the water content of by-product "B" to a level not conducive bacteria and fungi growth; i.e., less than about 12% water by weight. Such a by-product "B" can then be used in formulating various cosmetic and/or pharmaceutical products.

In a preferred embodiment a portion of the defatted soy solution from the microfiltration unit 30 is transferred via line 34 to a second extruder 35. In this embodiment of the invention additives via line 36 are mixed with the defatted soy solution in second extruder 35. The additives can include vitamins, minerals, amino acids, proteins, flavors, phytochemicals, pharmaceuticals, nutraceuticals, binders and fillers. It can also include other streams resulting from the treatment of carbohydrate-containing feedstock or processing of soybeans, or mixtures thereof.

In an alternate embodiment as described in more detail below and illustrated in FIG. 1 a nutrient-containing permeate stream from the treatment of the whole stillage can also be added via line 37 to the second extruder to thereby increase the nutritional content of the subsequently recovered by-products. In still another alternate embodiment the remaining portion of the defatted soy solution that is not feed to second extruder 35 can be transferred via line 38 to be mixed with the whole stillage for further processing as discussed below and illustrated in FIGS. 1 and 3.

It should be noted that use of microfiltration unit 30 to achieve a defatted soy solution is but one preferred method of producing the defatted soy solution. In an alternative preferred embodiment, the defatted soy solution can be produced directly by utilizing a commercially available soymeal that is already defatted and combining it with water and enzymes to form the desired soy solution.

In a preferred embodiment the extruded defatted soy solution is transferred via line 39 to first ultrafiltration unit 40 to form a nutrient-containing permeate stream and a soy protein retentate. The filter size of first ultrafiltration unit 40 is preferably sized and configured to have a molecular weight cut-off (MWCO) greater than about 1,000,000 to retain the soy protein from the extruded defatted soy solution. In a preferred embodiment the soy protein retentate is transferred via line 41 to dryer 42 where under time and temperature conditions a soy protein rich by-product "E" is formed and can be recovered via line 43. It is preferred that the operating conditions of dryer 42 be controlled to produce by-product "E" having less than about 12% water by weight. By-product "E" can then be used as a dietary nourishment value.

As illustrated in FIG. 2 the nutrient-containing permeate stream is preferably transferred via line 44 to a reverse osmosis filtration unit 45 designed to utilize high pressure (up to 5,000 psi or greater) and very small pore sizes to separate very low molecular weight materials, including vitamins, minerals, and soy carbohydrates, from the nutrient-containing permeate stream. These very low molecular weight materials are transferred via line 46 to dryer 47. It is preferred that the operating conditions of dryer 47 be controlled to produce by-product "I" having less than about 12% water by weight. The resulting by-product "I" can be recovered vial line 48 and used as a dietary supplement. The permeate (substantially water) from unit 45 can be re-circulated via line 49 to fermentation unit 8 or discharged into a water body, such as a lake, stream, or similar area.

In another preferred embodiment of the invention as illustrated in FIGS. 1 and 3, whole stillage from tank 15 is transferred via lines 50 and 51 to third extruder 52 or via lines 50 and 53 to second microfilter 54. Auxiliary nutrient containing materials or additives from line 55 are mixed with the whole stillage in extruder 52 to form an enhanced nutrient containing compound. The additives can be any ingredient in any amount that is needed to produce by-product "C" having the desired properties for its intended end use. Examples of such auxiliary nutrients include, but are not limited to, vitamins, minerals, amino acids, proteins, flavors, phytochemicals, pharmaceuticals, nutraceuticals, binders and fillers, other streams resulting from the treatment of carbohydrate-containing feedstock (such as the permeate from microfilter 54), streams resulting from the processing of soybeans (such as the full fat soy solution from mixer 25), as discussed below, and mixtures thereof.

The combined whole stillage and auxiliary materials are then extruded in the whole third extruder 52, under time, temperature, and pressure conditions to form an extruded compound. The extruded compound is transferred via line 56 to dryer 57 under time and temperature conditions to form a protein-rich nutrition by-product "C" having less than about 12% water by weight that can be recovered via line 58. By selection of the auxiliary materials by-product "C" will have an enhanced dietary nourishment value.

In another preferred embodiment, the remaining portion of the whole stillage not treated in the above discussed manner is transferred by line 53 to microfilter 54 to be further separated, based on molecular weight/particle size, into other value-added by-products. In this embodiment, microfilter 54 has a filter size of about 0.1 to 1.0 micron to produce a retentate stream, and a first nutrient-containing permeate stream. The permeate stream can be recycled via line 59 back to third extruder 52 to be thereby re-combined with the whole stillage and/or the other auxiliary materials indicated above. The filter size of the microfilter 54 should preferably be set to capture in the retentate stream various proteins and carbohydrates, fat globules, cell wall materials, and oils. These compounds all combine to form an emulsion that can be transferred by line 60 to dryer 61. It is preferred that the drying conditions be controlled to form by-product "D" having less than 12% water by weight. By-product "D" can be recovered by line 62 and used in the formulation of cosmetic and/or pharmaceutical products.

As indicated previously in another alternate preferred embodiment the first nutrient-containing permeate stream from the microfilter 54 can be transferred via line 37 to second extruder 35 where it is then combined with the defatted soy solution from microfilter 30 to thereby form a modified whole stillage stream that will increase the nutritional content of the subsequently recovered by-products "E" and "I", as discussed above, as well as by-products "F", "G" and "H" discussed below.

At this point, additional additives, such as vitamins, minerals, amino acids, proteins, flavors, phytochemicals, pharmaceuticals, nutraceuticals, binders, fillers, other streams resulting from the treatment of carbohydrate-containing feedstock, streams resulting from the processing of soybeans, and mixtures thereof, may also be introduced via line 63 to line 37 or via line 64 to line 39. Which additives and at what point in the process they are added is dependent on the particular by-products "E" through "I" that are desired.

Turning now to FIGS. 1 and 4 still another embodiment of the invention is illustrated. In this embodiment the permeate stream from line 37 is passed through additional filtering membranes for further separation into by-products "F" through "I". More particularly, the permeate from microfilter 54, with or without the permeate from second extruder 35, is transferred to ultrafiltration unit 65. As described above, additives from lines 63 or 64 can be introduced directly into the permeate stream 37 or stream 39 before it passes to ultrafiltration unit 65. If soybeans are not used in the process, then it is preferable that the additives from line 66 be added to line 67 feeding into ultrafiltration unit 65. The ultrafiltration units 65 and 68, nanofiltration unit 69 and reverse osmosis unit 45 will then be used to separate the protein materials of the additives from the non-protein components, and concentrate them along with the whole stillage proteins. After each stage of filtration, the resulting retentate streams are accumulated and transferred to dryers 70, 71, 72 and 47, respectively, via lines 73, 74, 75 and 46 whereby by-products "F", "G", "H" and "I", respectively, can be recovered from lines 76, 77, 78 and 48, respectively. Dryers 70, 71, 72 and 47, respectively, are operated under preferred time and temperature conditions, to create finished by-products with desirable functional characteristics. It is of course within the scope of this invention that one or more of the filtering units could be by-passed if a particular by-product is not desired.

In a preferred embodiment of the by-product recovery process, the nutrient-containing permeate stream from line 67 is then passed through ultrafiltration unit 65 to form another nutrient-containing permeate stream and another retentate stream. The filter size of ultrafiltration unit 65 is preferably sized and configured to have a molecular weight cut-off (MWCO) greater than 50,000 so as to retain the non-zein corn proteins in line 73 from the other nutrient-containing permeate in line 79. The non-zein protein retentate in line 73 is then dried under time and temperature conditions to form a non-zein rich product, referenced as by-product "F". The operating conditions in dryer 70 are controlled so that by-product "F" will have less than about 12% water by weight and will further have a flavor-enhancing value.

In another preferred embodiment the nutrient-containing permeate from ultrafiltration unit 65 will contain zein corn proteins. This permeate is then further passed via line 79 through ultrafiltration unit 68 to produce yet another nutrient-containing permeate stream and another retentate 61. Ultrafiltration unit 68 preferably comprises a filter membrane sized and configured to be of 10,000 MWCO to retain the zein corn proteins from the nutrient-containing permeate stream in line 79. The zein protein containing retentate in line 74 is subsequently dried under time and temperature conditions to produce a zein protein rich by-product "G". It is preferred that the operating conditions of dryer 71 be controlled to produce by-product "G" having less than about 12% water by weight and having a food coating value.

If specific carbohydrates are required, the nutrient-containing permeate in line 80 can be further passed through nanofiltration unit 69. The size of the filtering membrane is set to capture the particular carbohydrates desired. Examples would include various medium and low molecular weight destrins that can be used as a water soluble glue, as thickening agents in food processing, or as binding agents in pharmaceuticals. They can also be used in pyrotechnics to add color to the explosion bursts. In a preferred embodiment the filtering membrane of nanofiltration unit 69 is sized and configured to be of 10,000 MWCO or less in order to retain low and medium molecular weight dextrins that is recovered in line 75. The dextrins can then be dried in dryer 72 to form a dextrin by-product "H" having less than about 12% water by weight. These dextrins that can be used as water soluble glues, as thickening agents in agents in food processing, and as binding agents in pharmaceuticals. They can also be used in pyrotechnics to add color.

In another preferred embodiment a second enzyme (other than 1% alpha-amylase) is added to extruder 3 or elsewhere to promote the production of cyclodextrins during the fermentation step. This second enzyme is selected from those enzymes that are known to operate under the hydrolyzing and fermentation conditions and to do so in such a manner as not to interfere with the 1% alpha-amylase's production of ethanol. In this embodiment the filtering membrane of nanofiltration unit 69 is sized and configured to be of 2,000 MWCO in order to retain carbohydrates such as cyclodextrin that is recovered in line 75. The cyclodextrin retentate can then be dried in dryer 72 to form a cyclodextrin by-product "H" having less than about 12% water by weight that can be sold as a fiber source, and/or a carrier for organic chemicals, and/or a flavor source in the flavor industry. The cyclodextrins can also be used in analytical chemistry as a matrix for the separation of hydrophobic substances, as well as excipients in pharmaceutical formulations.

In another preferred embodiment additives such as those previously described can be added to one or more of the various permeate streams in lines 67, 79, 80 and 81 via lines 66, 82, 83 and 84, respectively, to further add nutrients or otherwise enhanced by-products "F", "G", "H" and "I", respectively. In another preferred embodiment each of the fully integrated soybean and corn feedstock processing steps set forth in FIG. 1 can be implemented so as to produce ethanol, as well as by-products "A" through "I".

While the invention has been described in terms of its preferred embodiments, other embodiments will be apparent to those of skill in the art from a review of the foregoing. Those embodiments as well as the preferred embodiments are intended to be encompassed by the scope and spirit of the following claims.

What we claim is:

1. A process for the production of ethanol and whole stillage from a carbohydrate-containing feedstock, comprising the steps of:
    a) milling the carbohydrate-containing feedstock to produce a carbohydrate-containing flour having a median particle size of less than about 100 microns;
    b) mixing water with the flour to produce a slurry solution;
    c) fermenting the slurry solution under fermentation conditions to produce a fermented product stream; and
    d) distilling the fermented product stream to produce an ethanol-rich stream and a separate whole stillage stream.

2. The process according to claim 1 wherein the slurry solution contains at least one enzyme in an amount of 0.5% to 1.5% by dry weight of the slurry solution; and the process further comprises, prior to fermentation, hydrolyzing the slurry stream at temperatures between about 80 C. and about 130 C. for a period of time between about 45 to about 60 seconds to produce a hydrolyzed slurry stream and fermenting the hydrolyzed slurry stream.

3. The process according to claim 2 wherein the carbohydrate containing feedstock is corn and wherein a de-hulled soy flour having a median particle size of less than about 100 microns is added to the hydrolyzed slurry stream.

4. The process according to claim 2 wherein the slurry solution contains an additive selected from the group consisting of vitamins, minerals, amino acids, proteins, flavors, phytochemicals, pharmaceuticals, nutraceuticals, binders and fillers and mixtures thereof.

5. The process according to claim 1 wherein the slurry solution contains an additive selected from the group consisting of vitamins, minerals, amino acids, proteins, flavors, phytochemicals, pharmaceuticals, nutraceuticals, binders and filler, and mixtures thereof.

6. The process according to claim 1 wherein a de-hulled soy flour having a median particle size of less than about 100 microns is added to the slurry solution.

7. A process for the production of ethanol and whole stillage from a carbohydrate-containing feedstock, comprising the steps of:
    a) milling the carbohydrate-containing feedstock to produce a milled feedstock having a median particle size of less than about 100 microns;
    b) mixing water and enzymes with the milled feedstock to produce a slurry solution, the enzymes comprising about 0.5% to about 1.5% by dry weight of the slurry solution;
    c) hydrolyzing the slurry solution;
    d) fermenting the hydrolyzed slurry solution under fermentation conditions to produce a fermented product stream; and
    e) distilling the fermented product steam to produce an ethanol-rich stream and a separate whole stillage stream.

8. The process according to claim 7 wherein the carbohydrate containing feedstock is corn and the hydrolyzing is for a period of time and under temperature and pressure conditions sufficient
    a) to partially gelatinize the milled feedstock to form corn starch molecules having terminal amylose groups; and
    b) to cleave at least some of the terminal amylose groups from the corn starch molecules.

9. The process according to claim 8 wherein the period of time and the temperature and pressure conditions are sufficient to cleave at least 20% of the terminal amylose groups from the corn starch molecules.

10. The process according to claim 9 wherein the hydrolyzing is conducted for a period of about 45-60 seconds and under moderate pressure and temperatures between about 80° C. and 130° C.

11. The process according to claim 7 wherein a de-hulled soy flour having a median particle size of less than about 100 microns is added to the hydrolyzed slurry stream.

12. The process according to claim 7 wherein a de-hulled soy flour having a median particle size of less than about 100 microns is added to the slurry solution.

13. A process for the production of ethanol and whole stillage from a carbohydrate-containing feedstock, consisting essentially of:
    a) milling the carbohydrate-containing feedstock to produce a carbohydrate-containing flour having a median particle size of less than about 100 microns;

b) mixing water with the flour to produce a slurry solution wherein the slurry solution contains at least one enzyme in an amount of 0.5% to 1.5% by dry weight of the slurry solution;

c) hydrolyzing the slurry stream at temperatures between about 80° C. and about 130° C. for a period of time between about 45 to about 60 seconds to produce a hydrolyzed slurry stream;

d) fermenting the slurry solution under fermentation conditions to produce a fermented product stream; and e) distilling the fermented product stream to produce an ethanol-rich stream and a separate whole stillage stream.

14. A process for the production of ethanol and whole stillage from a carbohydrate containing feedstock that increases the rate of production and volume of ethanol produced comprising milling the carbohydrate-containing feedstock to a particle size of less than about 100 microns, reducing the time for heating during hydrolysis, and increasing the level of amylose groups cleaved from the carbohydrate.

15. The process of claim 14 wherein reducing the time for heating comprises reducing the time to between about 45 to about 60 seconds.

16. The process of claim 14 wherein a conventional ethanol production process requires about 15 minutes for heating during hydrolysis and said reducing the time for heating comprises a reduction in the range of $\frac{1}{20}$ to $\frac{1}{15}$ of the time required for said conventional ethanol production process.

17. The process of claim 16 wherein said process further comprises fermentation and said reducing of time for heating causes the increase in the level of cleavage of amylose groups, and said increase in the level of cleavage of amylose groups increases the level of fermentation resulting in an increase in the volume of ethanol.

18. The process of claim 16 wherein said process further comprises fermentation and said reducing the time for heating further comprises an addition of pressure of about 500 psi and results in an increase in the number of cleaved amylose groups and an increase in the efficiency of fermentation and produce an increase in the volume of ethanol.

* * * * *